(12) United States Patent
Druma et al.

(10) Patent No.: US 11,484,355 B2
(45) Date of Patent: Nov. 1, 2022

(54) INFLATABLE BONE TAMP AND METHOD FOR USE OF INFLATABLE BONE TAMP

(71) Applicant: MEDTRONIC HOLDING COMPANY SÀRL, Tolochenaz (CH)

(72) Inventors: Calin Druma, San Jose, CA (US); Asha Sharma, San Jose, CA (US)

(73) Assignee: MEDTRONIC HOLDING COMPANY SÀRL, Tolochenaz (CH)

( * ) Notice: Subject to any disclaimer, the term of this patent is extended or adjusted under 35 U.S.C. 154(b) by 436 days.

(21) Appl. No.: 16/806,307

(22) Filed: Mar. 2, 2020

(65) Prior Publication Data

US 2021/0267657 A1   Sep. 2, 2021

(51) Int. Cl.
*A61B 17/88* (2006.01)

(52) U.S. Cl.
CPC ............................... *A61B 17/8855* (2013.01)

(58) Field of Classification Search
CPC .................................................. A61B 17/8855
See application file for complete search history.

(56) References Cited

U.S. PATENT DOCUMENTS

| | | |
|---|---|---|
| 3,211,150 A | 10/1965 | Foderick |
| 4,773,393 A | 9/1988 | Haber et al. |
| 4,921,483 A | 5/1990 | Wijay et al. |
| 5,057,106 A | 10/1991 | Kasevich et al. |
| 5,540,679 A | 6/1996 | Fram et al. |
| 5,843,116 A | 12/1998 | Crocker et al. |
| 6,129,737 A | 10/2000 | Hamilton et al. |
| 6,230,060 B1 | 5/2001 | Mawhinney |
| 6,241,727 B1 | 6/2001 | Tu |
| 6,352,551 B1 | 3/2002 | Wang |
| 6,364,900 B1 | 4/2002 | Heuser |
| 6,416,457 B1* | 7/2002 | Urick ................... A61N 5/1002 600/3 |
| 6,427,089 B1 | 7/2002 | Knowlton |
| 6,458,096 B1 | 10/2002 | Briscoe |
| 6,488,653 B1 | 12/2002 | Lombardo |
| 6,527,739 B1 | 3/2003 | Bigus et al. |
| 6,544,224 B1 | 4/2003 | Steese-Bradley |
| 6,847,848 B2 | 1/2005 | Sterzer et al. |
| 6,911,038 B2 | 6/2005 | Mertens |

(Continued)

FOREIGN PATENT DOCUMENTS

| | | |
|---|---|---|
| DE | 10010467 | 9/2001 |
| EP | 1313411 | 10/2007 |

(Continued)

OTHER PUBLICATIONS

International Search Report dated Aug. 8, 2017 of corresponding International Application No. PCT/US2017/029330.

(Continued)

*Primary Examiner* — Zade Coley

(57) ABSTRACT

An inflatable bone tamp including a first balloon portion and a second balloon portion is provided. Each of the first balloon portion and the second balloon portion include interior cavities that can be filled with liquid, and these interior cavities communicate with one another via a valve. The valve can limit or restrict flow of the liquid between the cavities. As such, the first balloon portion and the second balloon portion can be sequentially inflated with the liquid through use of the valve.

20 Claims, 10 Drawing Sheets

(56) References Cited

U.S. PATENT DOCUMENTS

| | | |
|---|---|---|
| 6,951,569 B2 | 10/2005 | Nohilly et al. |
| 7,197,363 B2 | 3/2007 | Prakash et al. |
| 7,261,720 B2 | 8/2007 | Stevens et al. |
| 7,537,580 B2 | 5/2009 | Willard |
| 7,826,904 B2 | 11/2010 | Appling et al. |
| 8,221,349 B2 | 7/2012 | Auyoung et al. |
| 8,241,335 B2 | 8/2012 | Truckai et al. |
| 8,382,746 B2 | 2/2013 | Williams |
| 8,679,106 B2 | 3/2014 | Ormsby |
| 8,708,955 B2 | 4/2014 | Tilson et al. |
| 8,945,107 B2 | 2/2015 | Buckley et al. |
| 2002/0120229 A1 | 8/2002 | Miles et al. |
| 2003/0130664 A1 | 7/2003 | Boucher et al. |
| 2003/0144298 A1 | 7/2003 | Curwen et al. |
| 2004/0092948 A1* | 5/2004 | Stevens ............... A61F 2/4601 606/96 |
| 2004/0106999 A1 | 6/2004 | Mathews |
| 2004/0133254 A1 | 7/2004 | Sterzer |
| 2004/0186471 A1 | 9/2004 | Trieu |
| 2005/0165389 A1 | 7/2005 | Swain |
| 2005/0245896 A1 | 11/2005 | Kucharczyk et al. |
| 2006/0034886 A1 | 2/2006 | Ward et al. |
| 2007/0149963 A1 | 6/2007 | Matsukuma et al. |
| 2008/0249604 A1 | 10/2008 | Donovan |
| 2009/0088788 A1* | 4/2009 | Mouw ............... A61B 17/8855 606/192 |
| 2009/0254064 A1 | 10/2009 | Boatman |
| 2009/0299327 A1* | 12/2009 | Tilson ............... A61B 17/8855 604/99.04 |
| 2009/0299373 A1 | 12/2009 | Sisken |
| 2009/0299401 A1* | 12/2009 | Tilson ............... A61B 17/8816 606/192 |
| 2010/0004650 A1 | 1/2010 | Ormsby |
| 2010/0321192 A1 | 12/2010 | Brannan |
| 2011/0028981 A1 | 2/2011 | McKay |
| 2011/0106184 A1 | 5/2011 | Sapida et al. |
| 2011/0125148 A1 | 5/2011 | Turner |
| 2011/0202064 A1 | 8/2011 | O'Halloran et al. |
| 2011/0319880 A1 | 12/2011 | Prakash |
| 2012/0165941 A1 | 6/2012 | Rabiner |
| 2012/0197319 A1 | 8/2012 | Auyoung et al. |
| 2012/0197321 A1 | 8/2012 | Donovan |
| 2012/0203220 A1 | 8/2012 | Brannan et al. |
| 2012/0259326 A1 | 10/2012 | Brannan |
| 2012/0296273 A1 | 11/2012 | Arana et al. |
| 2013/0053880 A1 | 2/2013 | Bouasaysy et al. |
| 2013/0144298 A1 | 6/2013 | Choi |
| 2013/0237950 A1 | 9/2013 | Gianotti |
| 2013/0238038 A1 | 9/2013 | Auyoung |
| 2013/0256302 A1 | 10/2013 | Chu |
| 2013/0261729 A1 | 10/2013 | Gillick et al. |
| 2013/0304182 A1 | 11/2013 | Pacetti et al. |
| 2014/0128877 A1 | 5/2014 | O'Halloran |
| 2014/0276572 A1 | 9/2014 | Auyoung et al. |
| 2014/0277466 A1* | 9/2014 | Teisen ............... A61F 2/441 623/17.12 |
| 2014/0303633 A1 | 10/2014 | O'Halloran et al. |
| 2014/0303730 A1 | 10/2014 | McGuire et al. |
| 2014/0316411 A1 | 10/2014 | Day |
| 2014/0371652 A1* | 12/2014 | Aramaki ............... A61F 5/0076 604/8 |
| 2014/0371672 A1 | 12/2014 | Pinchuk et al. |
| 2015/0342660 A1 | 12/2015 | Nash |
| 2015/0359432 A1 | 12/2015 | Ehrenreich |
| 2017/0367747 A1* | 12/2017 | Druma ............... A61B 17/8855 |
| 2019/0110826 A1 | 4/2019 | Goshayeshgar et al. |

FOREIGN PATENT DOCUMENTS

| | | |
|---|---|---|
| EP | 2853210 | 4/2015 |
| WO | 217801 A2 | 3/2002 |
| WO | 217801 A3 | 3/2002 |
| WO | 2006053312 | 5/2006 |
| WO | 2008026888 | 3/2008 |
| WO | 2013074933 | 5/2013 |

OTHER PUBLICATIONS

Supplementary European Search Report dated Jul. 11, 2018 of corresponding European Application No. 16735443.0.

European Search Search and Opinion for EP17177266 the counterpart application dated Nov. 16, 2017, 9 pages.

Supplementary European Search Report dated Nov. 18, 2019 of corresponding European Application No. 17790239.2.

Examination Report dated Jan. 28, 2021 of European Application No. 17790239.2.

International Search Report and Written Opinion dated May 6, 2021 of International Application No. PCT/US2021/019442.

\* cited by examiner

INFLATABLE BONE TAMP AND METHOD FOR USE OF INFLATABLE BONE TAMP

FIELD

The present technology generally relates to an inflatable bone tamp and a method of using an inflatable bone tamp.

BACKGROUND

Wedge fractures are compression fractures of vertebral bodies. Such wedge fractures result in a lateral portion, an anterior portion, or a posterior portion of an endplate being displaced from its normal configuration. And such displacement causes misalignment of such an endplate with the opposing endplate across a disk space. The misalignment of the opposing endplates can cause misalignment of the corresponding adjacent vertebrae with respect to one another. To facilitate use of surgical solutions to ameliorate a wedge fracture, an anatomically-correct relationship between the adjacent vertebrae should first be restored. Therefore, there is a need for a device such as an inflatable bone tamp that can accommodate the displaced portion of the endplate of a vertebrae to facilitate restoration of an anatomically-correct relationship with an adjacent vertebrae across the disc space therebetween.

SUMMARY

The techniques of this disclosure generally relate to an inflatable bone tamp having at least sequentially inflatable first and second balloon portions used to facilitate in correcting spinal deformities.

In one aspect, the present disclosure provides an inflatable bone tamp including an inner first tubular portion including a first passageway therethrough, and extending between a first proximal end and an opposite first distal end, the inner first tubular portion including at least one aperture adjacent the first distal end; an outer second tubular portion including a second passageway therethrough, and extending between a second proximal end and an opposite second distal end, the inner first tubular portion extending through the second passageway; a valve including an outer surface, a first side, an opposite second side, an aperture extending between the first side and the second side, and various perforations extending between the first side and the second side, the inner first tubular portion being received through the aperture; a first balloon portion including a first cavity, a first distal end portion, and a first proximal end portion, the first distal end portion being attached relative to the inner first tubular portion, and the first proximal end portion being attached relative to the outer surface of the valve; and a second balloon portion including a second cavity, a second distal end portion, and a second proximal end portion, the second distal end portion being attached relative to the outer surface of the valve, and the second proximal end portion being attached relative to the outer second tubular portion; where the first cavity and the second cavity communicate with one another via the various perforations in the valve, where a liquid pumped through the first passageway can enter the first cavity via the at least one aperture of the inner first tubular portion and can expand the first balloon portion from a first contracted position to a first expanded position, where the valve limits passage of the liquid from the first cavity to the second cavity through the various perforations until a threshold pressure of the liquid is reached in the first cavity, and where the fluid entering the second cavity via the various perforations in the valve can expand the second balloon portion from a second contracted position to a second expanded position.

In one aspect, the present disclosure provides an inflatable bone tamp including an outer first tubular portion including a first passageway therethrough, and extending between a first proximal end and an opposite first distal end; an inner second tubular portion including a second passageway therethrough, and extending between a second proximal end and an opposite second distal end, the inner second tubular portion extending through the first passageway, and the inner second tubular portion including at least one aperture adjacent the first distal end; a valve including an outer surface, a first side, an opposite second side, an aperture extending between the first side and the second side, and various perforations extending between the first side and the second side, the inner second tubular portion being received through the aperture; a first balloon portion including a first cavity, a first proximal end portion, and a first distal end portion, the first proximal end portion being attached relative to the outer first tubular portion, and the first distal end portion being attached relative to the outer surface of the valve; and a second balloon portion including a second cavity, a second proximal end portion, and a second distal end portion, the second proximal end portion being attached relative to the outer surface of the valve, and the second distal end portion being attached relative to the inner second tubular portion; where the first cavity and the second cavity communicate with one another via the various perforations in the valve, where a liquid pumped through the first passageway can enter the first cavity and can expand the first balloon portion from a first contracted position to a first expanded position, where the valve limits passage of the liquid from the first cavity to the second cavity through the various perforations until a threshold pressure of the liquid is reached in the first cavity, and where the fluid entering the second cavity via the various perforations in the valve can expand the second balloon portion from a second contracted position to a second expanded position.

In one aspect, the present disclosure provides an inflatable bone tamp including an inner first tubular portion including a first passageway therethrough, and extending between a first proximal end and an opposite first distal end, the inner first tubular portion including at least one aperture adjacent the first distal end; an outer second tubular portion including a second passageway therethrough, and extending between a second proximal end and an opposite second distal end, the inner first tubular portion extending through the second passageway; a valve including an outer surface, a first side, an opposite second side, an aperture extending between the first side and the second side, and various perforations extending between the first side and the second side, the inner first tubular portion being received through the aperture; a first balloon portion having a first distal end portion and a first proximal end portion, the first distal end portion being attached relative to the inner first tubular portion, and the first proximal end portion being attached relative to the outer surface of the valve; and a second balloon portion having a second distal end portion and a second proximal end portion, the second distal end portion being attached relative to the outer surface of the valve, and the second proximal end portion being attached relative to the outer second tubular portion; where interiors of the first balloon portion and the second balloon portion communicate with one another via the various perforations in the valve, where a liquid pumped through the first passageway can enter the interior of the first balloon portion via the at least one aperture of the inner first tubular portion and can expand the first balloon portion from a first contracted position to a first expanded position, where the valve limits passage of the liquid between the interiors of the first balloon portion and the second balloon portion through the various perforations until a threshold pressure of the liquid is reached in the interior of the first balloon portion, and where the fluid entering the interior of the second balloon portion via the various perforations in the valve can expand the second balloon portion from a second contracted position to a second expanded position.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The techniques of this disclosure generally relate to an inflatable bone tamp including a first balloon portion and a second balloon portion that are sequentially inflatable.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
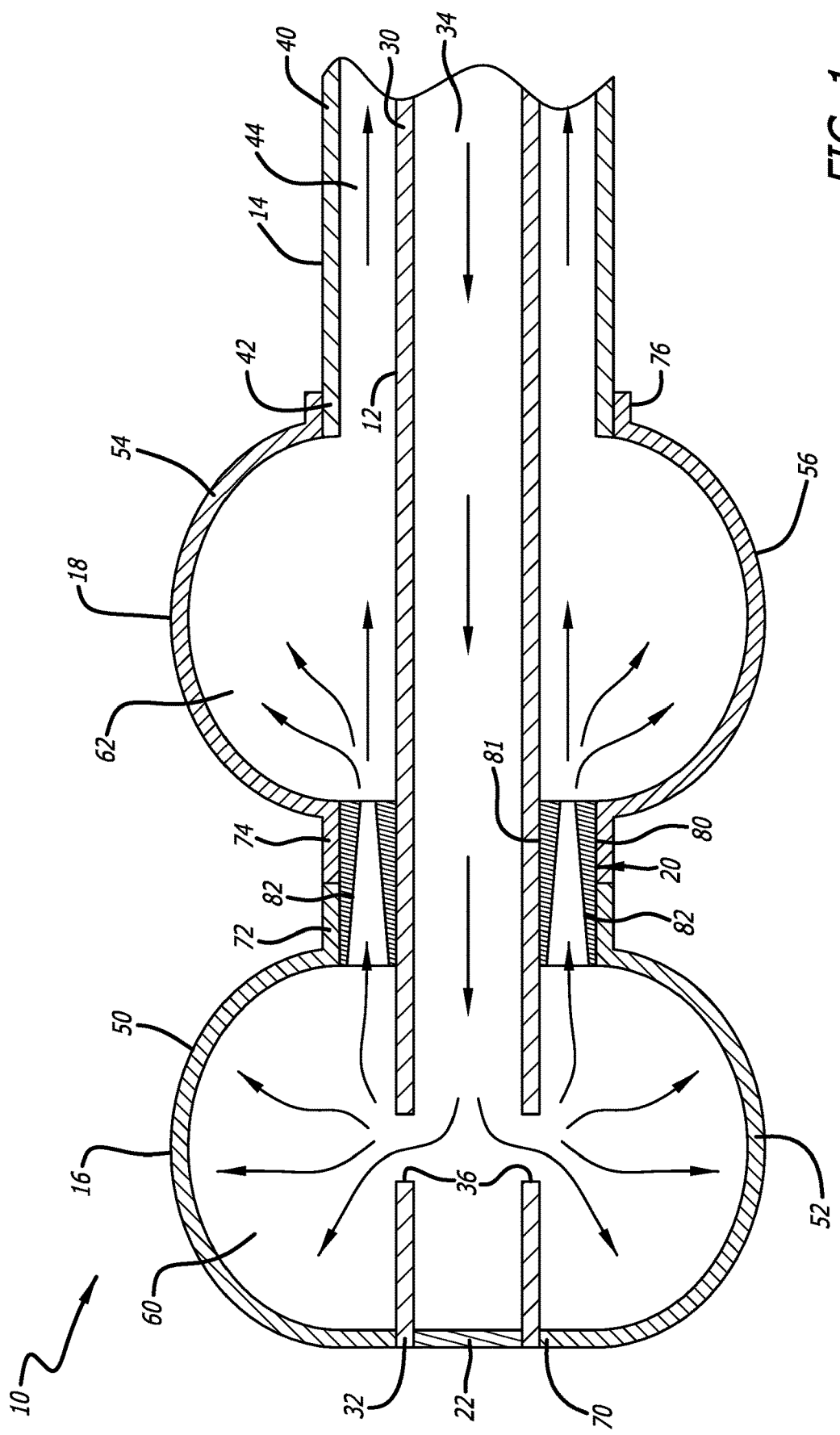
FIG. 1 is a side, cross-sectional, elevational view that illustrates an inflatable bone tamp including a first balloon portion and a second balloon portion that are sequentially inflatable.
Figure 2:
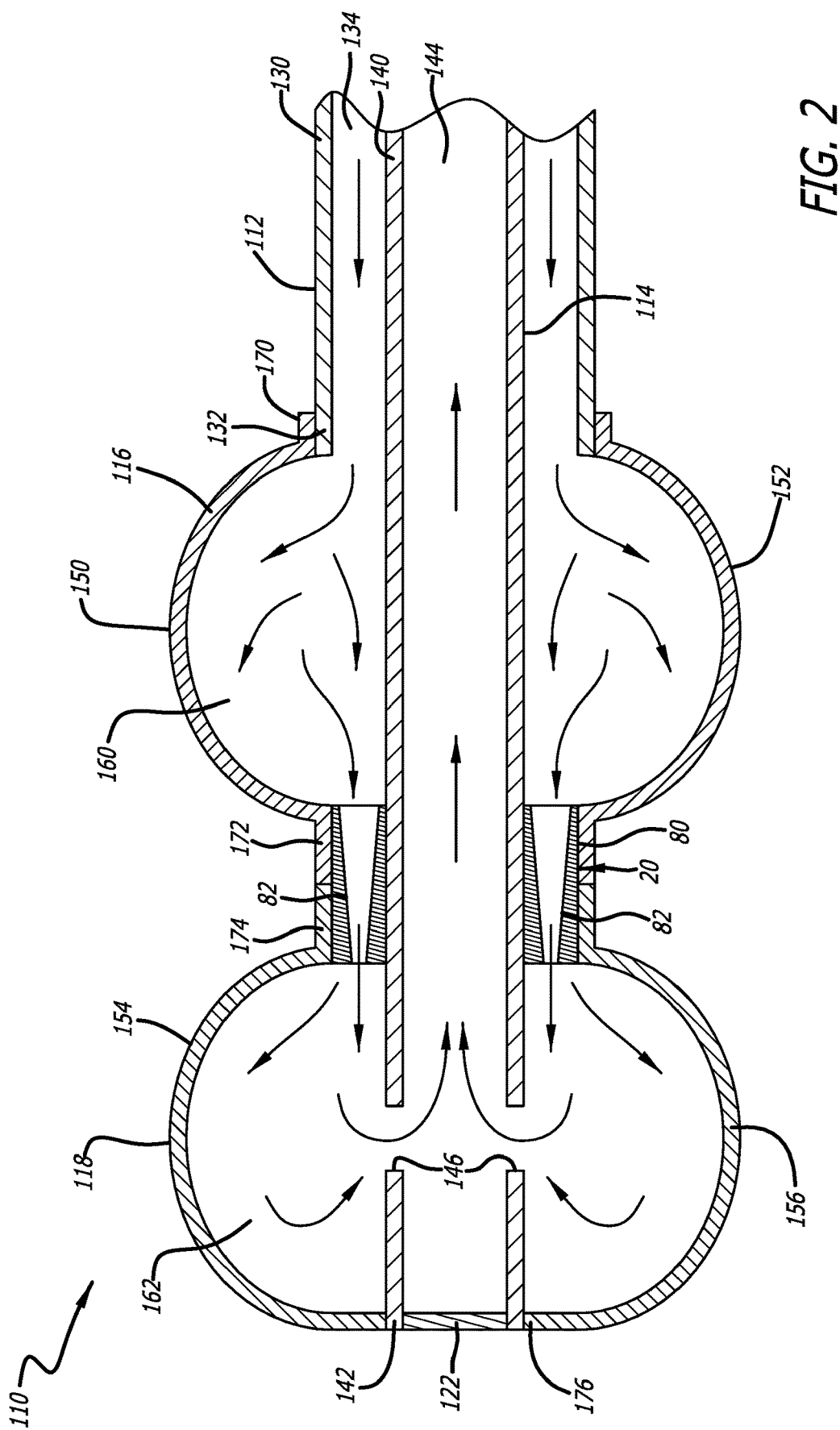
FIG. 2 is a side, cross-sectional, elevational view that illustrates another inflatable bone tamp including a first balloon portion and a second balloon portion that are sequentially inflatable.

FIGS. 1 and 2 each depict an embodiment of an inflatable bone tamp generally indicated by the numerals 10 and 110, respectively. The inflatable bone tamps 10 and 110 each include at least two balloon portions that can be sequentially inflated. As discussed below, such sequential inflation can be used in creating anatomical relationships between adjacent vertebrae that can used to facilitate repair thereof.

As depicted in FIG. 1, the inflatable bone tamp 10 includes an inner first tubular (or shaft) portion 12, an outer second tubular (or shaft) portion 14, a first balloon portion 16, a second balloon portion 18, a valve 20, an end cap 22, an inflation port (not shown), a deflation port (not shown), a first pump (not shown), and a second pump (not shown). The first balloon portion 16 and the second balloon portion 18 can be made of elastomeric materials facilitating expansion and contraction thereof. The inflation port is attached to or formed relative to the inner first tubular portion 12, the deflation port is attached to or formed with the outer second tubular portion 14, the first pump is used in supplying a liquid to the first balloon portion 16 and the second balloon portion 18 via the inflation port and the inner first tubular portion 12, and the second pump is used in both providing back pressure to facilitate inflation of the first balloon portion 16 and the second balloon portion 18, and removing the liquid from the first balloon portion 16 and the second balloon portion 18 via the deflation port and the outer second tubular portion 14. The liquid supplied to the first balloon portion 16 and the second balloon portion 18 can be a contrast medium that is a saline-based liquid solution.

The inner first tubular portion 12 can have a cylindrical outer shape, and includes a proximal end 30, an opposite distal end 32, and a passageway (or lumen) 34 that extends from the proximal end 30 to at least adjacent the distal end 32. Although not shown, the inflation port is operatively connected to the first pump, and the inflation port is also attached to or formed relative to the inner first tubular portion 12 at or adjacent the distal end 32. As depicted in FIG. 1, the passageway 34 terminates adjacent the distal end 32 at the end cap 22 that can be attached to inner first tubular portion 12. Alternatively, the inner first tubular portion 12 can have a blind end (not shown) at the distal end 32 that is integrally formed therewith. The inner first tubular portion 12 includes apertures 36 therein adjacent the distal end 32, and as discussed below, the apertures 36 allow fluid to exit the passageway 34 and enter the first balloon portion 16.

The outer second tubular portion 14 can have a cylindrical outer shape, and includes a proximal end 40, an opposite distal end 42, and passageway (or lumen) 44 extends from the proximal end 40 to the distal end 42. Although not shown, the deflation port is operatively connected to the second pump, and the deflation port is attached to or formed relative to the outer second tubular portion 14 at or adjacent the distal end 42. As depicted in FIG. 1, the inner first tubular portion 12 extends through the passageway 44, and the distal end 42 can be attached to the second balloon portion 18.

The first balloon portion 16 and the second balloon portion 18, as depicted in FIG. 1, are positioned around at least portions of the inner first tubular portion 12. The first balloon portion 16 is positioned distally of the second balloon portion 18 relative to the inner first tubular portion 12. The first balloon portion 16 and the second balloon portion 18 can have complete toroidal or partial toroidal shapes that extend around the inner first tubular portion 12. As discussed below, each of the first balloon portion 16 and the second balloon portion 18 are expandable/deflatable between a contracted first position and an expanded second position.

As depicted in FIG. 1, the first balloon portion 16 in cross-section includes a first lobular portion 50 and a second lobular portion 52, and the second balloon portion 18 in cross-section includes a first lobular portion 54 and a second lobular portion 56. The first balloon portion 16 includes a first interior cavity 60 (which, because the first balloon portion 16 is toroidal, is depicted in each of the first lobular portion 50 and the second lobular portion 52). Furthermore, the second balloon portion 18 includes a second interior cavity 62 (which, because the second balloon portion 18 is toroidal, is depicted in each of the first lobular portion 54 and the second lobular portion 56. As discussed below, the first interior cavity 60 and the second interior cavity 62 are fillable with a liquid to facilitate expansion of the first balloon portion 16 and the second balloon portion 18 from the contracted first position to the expanded second position.

The first balloon portion 16 includes a distal end portion 70 and a proximal end portion 72, and the second balloon portion 18 includes a distal end portion 74 and a proximal end portion 76.

The distal end portion 70 of the first balloon portion 16 can be annular (given that the outer shape of inner first tubular portion 12 is cylindrical), is attached relative to the inner first tubular portion 12, and is configured to facilitate formation of a fluid tight seal to prevent the liquid received in the first interior cavity 60 from escaping.

The proximal end portion 72 of the first balloon portion 16 can also be annular (given that the outer shape of the valve 20 is cylindrical), is attached relative to the valve 20 (which is attached relative to the inner first tubular portion 12, and is configured to facilitate formation of a fluid tight seal to prevent the liquid received in the first interior cavity 60 from escaping.

The distal end portion 74 of the second balloon portion 18 can be annular (given that the outer shape of the valve 20 is cylindrical), is attached relative to the valve 20, and is configured to facilitate formation of a fluid tight seal to prevent liquid received in the second interior cavity 62 from escaping.

The proximal end portion 76 of the second balloon portion 18 can be annular (given that the outer shape of the outer second tubular portion 14 is cylindrical), is attached relative to the outer second tubular portion 14, and is configured to facilitate formation of a fluid tight seal to prevent the liquid received in the second interior cavity 62 from escaping.

So long as a fluid tight seal is formed therebetween, the distal end portion 70 can be directly or indirectly attached to the inner first tubular portion 12, the proximal end portion 72 can be directly or indirectly attached to the valve 20, the distal end portion 74 can be directly or indirectly attached to the valve 20, and the proximal end portion 76 can be directly or indirectly attached to the outer second tubular portion 14. The direct or indirect attachment can be effectuated using adhesives, heat welding, mechanical fasteners, and/or complimentary surface configurations formed on mating components. Furthermore, while the inner first tubular portion 12, the outer second tubular portion 14, and the valve 20 have cylindrical outer shapes, these components can have different outer shapes, and the distal end portion 70, the proximal end portion 72, the distal end portion 74, and the proximal end portion 76 can be configured to compliment these different shapes.

Figure 3:
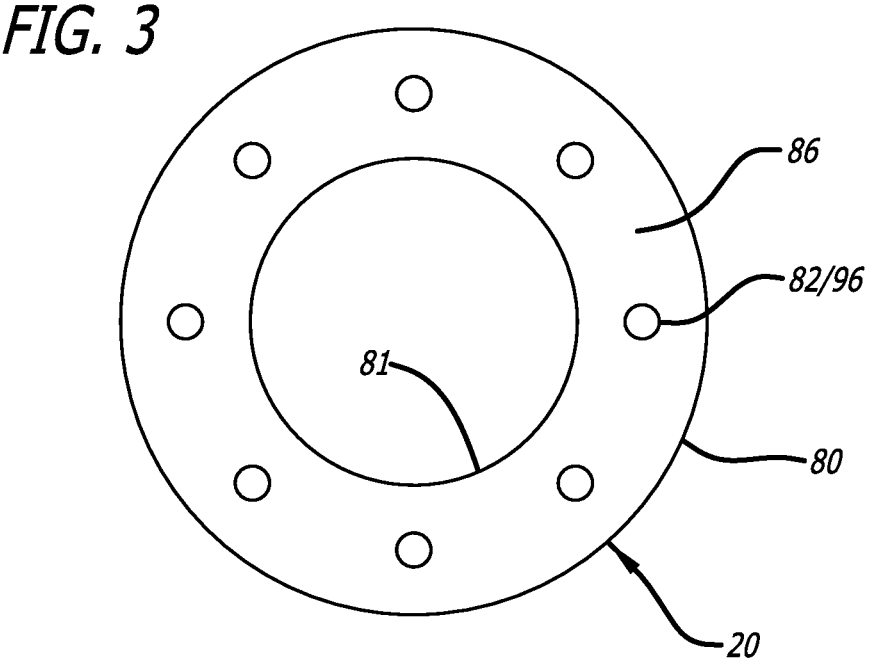
FIG. 3 is a front, elevational view that illustrates a valve for use with the inflatable bone tamps of FIGS. 1 and 2.

As depicted in FIGS. 1 and 3, the valve 20 can have a cylindrical outer surface 80, and includes an aperture 81 extending therethrough between a first side 84 and a second side 86. The aperture 81 is sized to receive the inner first tubular portion 12 therein and form a fluid tight seal therebetween, and the aperture 81 is cylindrical because inner first tubular portion 12 is also cylindrical. Furthermore, while the inner first tubular portion 12 has a cylindrical outer shape, the inner first tubular portion 12 can have different outer shapes, and the aperture 81 of the valve 20 can be configured to compliment these different shapes.

Figure 4:
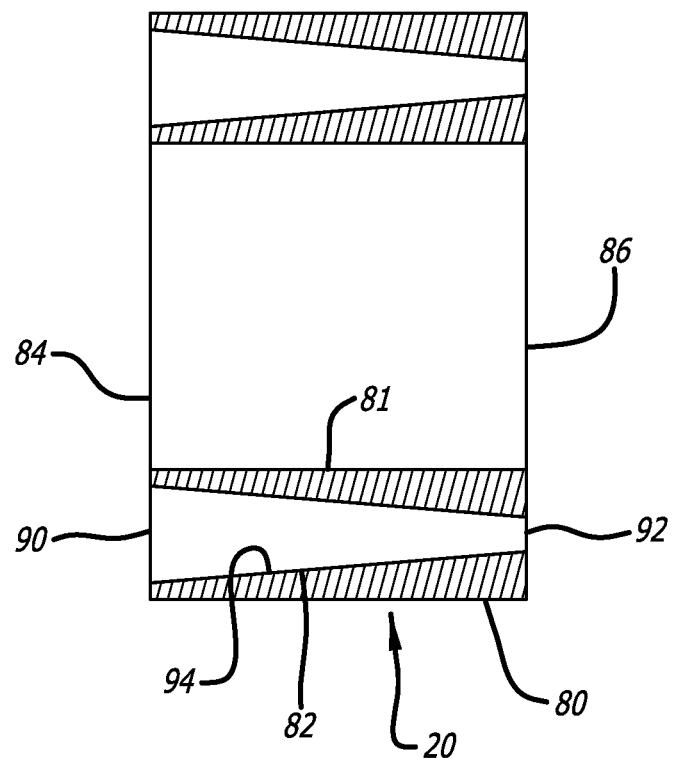
FIG. 4 is a side, cross-sectional, elevational view that illustrates the valve of FIG. 3.

The valve 20 includes various perforations (or channels) 82 that, like the aperture 81, extend between the first side 84 and the second side 86. The perforations 82 serve as restrictions used to limit flow of liquid through the valve 20 by creating a large pressure drop between the first side 84 and the second side 86. The pressure drop can range from 50 to 300 psi. As depicted in FIG. 4, the perforations 82 include a relatively large first opening 90 adjacent the first side 84, a relatively small second opening 92 adjacent the second side 86, and a pathway 94 formed as a tapered area between the first opening 90 and the second opening 92. As discussed below, when using the inflatable bone tamp 10, the configurations of the perforations 82 require that a liquid be at an elevated threshold pressure that can range from 50 to 300 psi to pass from the first side 84 to the second side 86 of the valve 20 through the perforations. Furthermore, the pressure drop and the corresponding threshold pressure can be calibrated by the configuration of the perforations 82. As such, the perforations 82 serve in restricting the passage of fluid from the first cavity 60 until the pressure of the fluid in the first cavity 60 meets and exceeds the threshold pressure.

Figure 5:
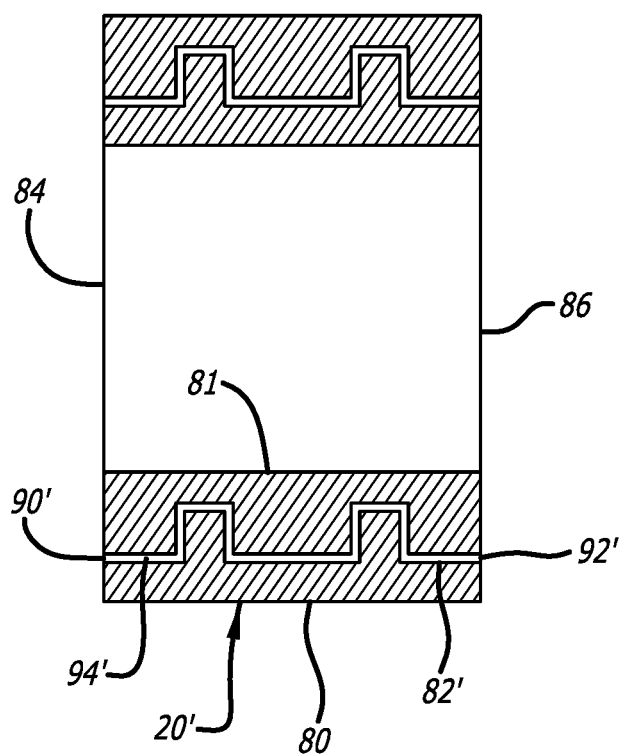
FIG. 5 is a side, cross-sectional, elevational view that illustrates another valve for use with the bone tamps of FIGS. 1 and 2.
Figure 6:
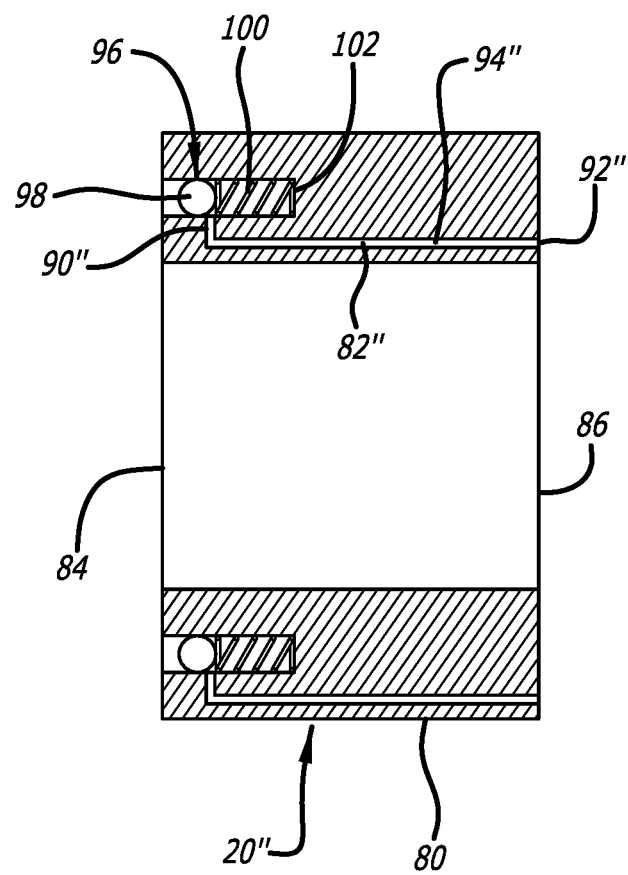
FIG. 6 is a side, cross-sectional, elevational view that illustrates yet another valve for use with the bone tamps of FIGS. 1 and 2.
Figure 7:
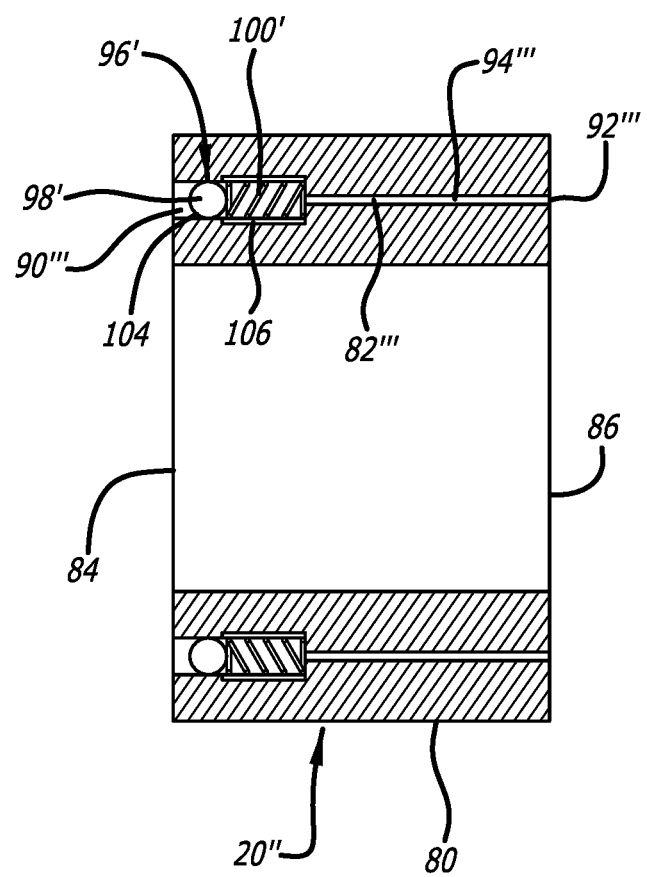
FIG. 7 is a side cross-sectional, elevational view that illustrates yet another valve for use with the bone tamps of FIGS. 1 and 2.

FIGS. 5, 6, and 7 disclose additional configurations of valves that can be used alternatively to the valve 20. FIG. 5 depicts a valve 20' including the outer surface 80, the aperture 81, the first side 84, the second side 86, and identical exterior dimensions to the valve 20. Rather than the perforations 82, the valve 20' includes perforations (or channels) 82' having a first opening 90' on the first side 84, a second opening 92' on the second side 86, and a pathway 94' extending between the first opening 90' and the second opening 92'. The first and second openings 90' and 92' can be of similar dimensions, and the pathway 94' is convoluted or tortured passage therebetween. Like the valve 20, because of the large pressure drop between the first side 84 and the second side 86 ranging from 50 to 300 psi created by the convoluted or tortured passage of the perforations 82', a liquid at the threshold pressure ranging from 50 to 300 is required to pass from the first side 84 to the second side 86 of the valve 20' through the perforations 82'. Like the valve 20, the pressure drop and the corresponding threshold pressure can be calibrated by the configuration of the perforations 82'.

FIG. 6 depicts a valve 20" including the outer surface 80, the aperture 81, the first side 84, the second side 86, and identical exterior dimensions to the valves 20 and 20'. Rather than the perforations 82 and 82', the valve 20" includes perforations (or channels) 82" each having a first opening 90" adjacent the first side 84, a second opening 92" on the second side 86, and a pathway 94" extending between the first and second openings 90" and 92". The perforations 82" are used in association with check valves 96. The check valves 96 each include a ball 98 and a spring 100 that are received in a recess 102. The recesses 102 are formed in the first side 84 and communicate with the perforations 82". For each of the check valves 96, the spring 100 is biased to maintain the ball 98 in position covering the first opening 90", and a liquid at the threshold pressure is required to move the ball 98 by overcoming the bias of the spring 100. When the ball 98 is moved away from first opening 90", a liquid can enter the perforation 82 from the recess 102 to travel from the first side 84 to the second side 86. Like the valves 20 and 20', because of the large pressure drop between the first side 84 and the second side 86 ranging from 50 to 300 psi created by the check valves 96, a fluid at the threshold pressure ranging from 50 to 300 psi is required to pass from the first side 84 to the second side 86 of the valve 20″ through the perforations 82″. The pressure drop and the corresponding threshold pressure can be calibrated by the configuration of the check valves 96. To increase the pressure drop and the corresponding threshold pressure, a stiffer spring 100 can be used, and to decrease the pressure drop and the corresponding threshold pressure, a softer spring 100 can be used.

FIG. 7 depicts a valve 20‴ including the outer surface 80, the aperture 81, the first side 84, the second side 86, and identical exterior dimensions to the valves 20, 20′, and 20″. The valve 20‴ includes perforations (or channels) 82‴ that incorporate a smaller first recess portion 104 and a larger second recess portion 106, and each of the perforations 82‴ includes a first opening 90‴ adjacent the first side 84, a second opening 92‴ adjacent the second side 86, and a pathway 94‴ extending between the first opening 90‴ and 92‴. Similar to the valve 20″, the valve 20‴ incorporates check valves 96′ that each include a ball 98′ and spring 100′ that are received in the first recess portion 104 and/or the second recess portion 106. For each of the check valves 96′, the spring 100′ is biased to maintain the ball 98′ in position covering the first opening 90‴, and a liquid at the threshold pressure is required to move the ball 98′ by overcoming the bias of the spring 100′. When the ball 98 is moved away from the first opening 90‴, travels from the first recess portion 104 to the second recess portion 106, a liquid can pass from the first recess portion 104 into the second recess portion 106 (because the second recess portion 106 is larger than the first recess portion 104), and then pass through the remainder of the perforation 82 to travel from the first side 84 to the second side 86. Like the valves 20, 20′, and 20″, because of the large pressure drop between the first side 84 and the second side 86 ranging from 50 to 300 psi created by the check valves 96′, a fluid at the threshold pressure ranging from 50 to 300 psi is required to pass from the first side 84 to the second side 86 of the valve 20‴ through the perforations 82‴. The pressure drop and the corresponding threshold pressure can be calibrated by the configuration of the check valves 96′. To increase the pressure drop and the corresponding threshold pressure, a stiffer spring 100′ can be used, and to decrease the pressure drop and the corresponding threshold pressure, a softer spring 100′ can be used.

Figure 8:
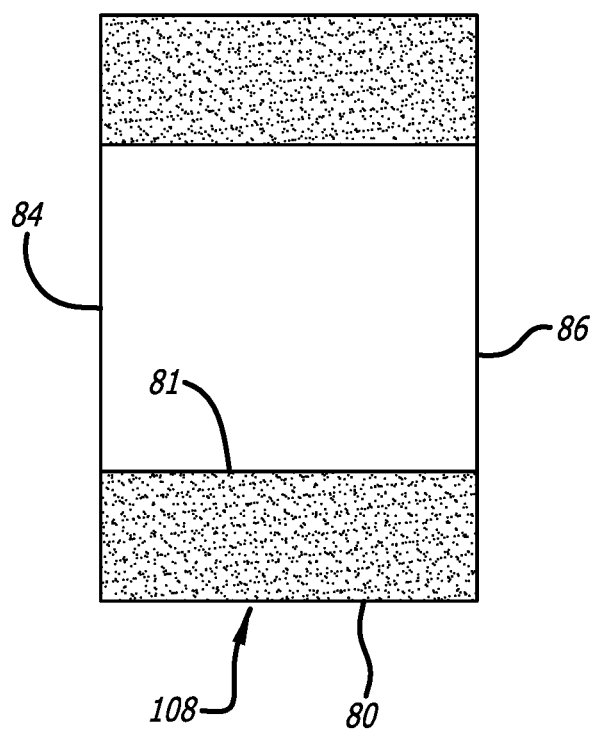
FIG. 8 is a side, cross-sectional, elevational view that illustrates yet another valve for use with the bone tamps of FIGS. 1 and 2.

FIG. 8 depicts a valve 108 including the outer surface 80, the aperture 81, the first side 84, the second side 86, and identical exterior dimensions to the valves 20, 20′, 20″, and 20‴. Rather than the perforations 82, 82′, 82″, and 82‴, the valve 108 is made of a foam such as an open-cell foam that permits fluid at the threshold pressure to pass therethrough through various perforations formed through the cell structure of the foam. The foams used for the valve 108 can include polyurethane foams, plastic, metallic, and/or composite foams. Like the valves 20, 20′, 20″, and 20‴, a fluid at the threshold pressure is required to pass from the first side 84 to the second side 86 of the valve 108 through the foam. The pressure drop and the corresponding threshold pressure can be calibrated by the type and/or the configuration of the foam.

During use thereof, first balloon portion 16 and the second balloon portion 18 of the inflatable bone tamp 10 can be positioned in a surgical area. Thereafter, the liquid is first pumped through the passageway 34 formed in the inner first tubular portion 12 by the first pump. The liquid exits the passageway 34 and enters the first balloon portion 16 via the apertures 36 formed adjacent the distal end 32 of the inner first tubular portion 12. After exiting the apertures 36, the liquid fills the first interior cavity 60 to expand the first balloon portion 16 from the contracted first position to the expanded second position. After the pressure of the liquid reaches the threshold pressure, the first balloon portion 16 stops expanding and the liquid is forced through the perforations 82 to enter the second interior cavity 62 of the second balloon portion 18 to expand the second balloon portion 18 from the contracted first position to the expanded second position. As such, the first balloon portion 16 and the second balloon portion 18 are inflated sequentially, with the first balloon portion 16 being inflated first and the second balloon portion 18 being inflated second via use of the valve 20. The valves 20′, 20″, 20‴, and 108 can be used in identical fashion to sequentially inflate the first balloon portion 16 and the second balloon portion 18. Furthermore, the expanded second position of the second balloon portion 18 can vary as needed to afford different amounts of expansion thereof.

After use of the inflatable bone tamp 10 is nearing completion, the first pump can be reversed to pump liquid from the first interior cavity 60 of the first balloon portion 16 via the apertures 36 and the passageway 34 of the inner first tubular portion 12, and the second pump can be used to pump liquid from the second interior cavity 62 of the second balloon portion 18 via the passageway 44 of the outer second tubular portion 14. After being deflated, the inflatable bone tamp 10 can be removed from the surgical area.

As depicted in FIG. 2, the inflatable bone tamp 110 includes an outer first tubular (or shaft) portion 112, an inner second tubular (or shaft) portion 114, a first balloon portion 116, a second balloon portion 118, the valve 20, an end cap 122, an inflation port (not shown), a deflation port (not shown), a third pump (not shown), and a fourth pump (not shown). The valve 20 for the inflatable bone tamp 110, as depicted in FIG. 2, is reversed in orientation from that depicted in FIG. 1 for the inflatable bone tamp 10. The first balloon portion 116 and the second balloon portion 118 can be made of elastomeric materials facilitating expansion and contraction thereof. The inflation port is attached to or formed relative to the outer first tubular portion 112, the deflation port is attached to or formed relative to the inner second tubular portion 114. The third pump is used in supplying a liquid to the first balloon portion 116 and the second balloon portion 118 via the inflation port and the outer first tubular portion 112, and the fourth pump is used in both providing back pressure to facilitate inflation of the first balloon portion 116 and the second balloon portion 118, and removing the liquid from the first balloon portion 116 and the second balloon portion 118 via the deflation port and the inner second tubular portion 114. As discussed above, the liquid supplied to the first balloon portion 116 and the second balloon portion 118 can be a contrast medium that is a saline-based liquid solution.

The outer first tubular portion 112 can have a cylindrical outer shape, and includes a proximal end 130, an opposite distal end 132, and a passageway (or lumen) 134 that extends from the proximal end 130 to the distal end 132. Although not shown, the inflation port is operatively connected to the third pump, and the inflation port is also attached to or formed relative to the outer first tubular portion 112 at or adjacent the distal end 142. As depicted in FIG. 2, the second inner tubular portion 114 extends through the passageway 134, and the distal end 132 can be attached to the first balloon portion 116.

The inner second tubular portion 114 can have a cylindrical outer shape, and includes a proximal end 140, an opposite distal end 142, and passageway (or lumen) 144 extends from the proximal end 140 to the distal end 142. Although not shown, the deflation port is operatively connected to the fourth pump, and the deflation port is also attached to or formed relative to the inner second tubular portion 114 at or adjacent the distal end 142. As depicted in FIG. 2, the passageway 144 terminates adjacent the distal end 142 at the end cap 122 that can be attached to the inner second tubular portion 114. Alternatively, the inner second tubular portion 114 can have a blind end (not shown) at the distal end 142. The inner second tubular portion 114 includes apertures 146 therein adjacent the distal end 142, and as discussed below, the apertures 146 allow fluid to exit the second balloon portion 118 and enter the passageway 144.

The first balloon portion 116 and the second balloon portion 118, as depicted in FIG. 2, are positioned around at least portions of the inner second tubular portion 114. The first balloon portion 116 is positioned proximately of the second balloon portion 118 relative to the inner second tubular portion 114. The first balloon portion 116 and the second balloon portion 118 can have complete toroidal or partial toroidal shapes that extend around the inner second tubular portion 114. As discussed below, each of the first balloon portion 116 and the second balloon portion 118 are expandable/deflatable between a contracted first position and an expanded second position.

In the cross-section of FIG. 2, the first balloon portion 116 includes a first lobular portion 150 and a second lobular portion 152, and the second balloon portion 118 includes a first lobular portion 154 and a second lobular portion 156. The first balloon portion 116 includes a first interior cavity 160 (which, because the first balloon portion 116 is toroidal, is depicted in each of the first lobular portion 150 and the second lobular portion 152). Furthermore, the second balloon portion 118 includes a second interior cavity 162 (which, because the second balloon portion 118 is toroidal, is depicted in each of the first lobular portion 154 and the second lobular portion 156. As discussed below, the first interior cavity 160 and the second interior cavity 162 are fillable with a liquid to facilitate expansion of the first balloon portion 116 and the second balloon portion 118 from the contracted first position to the expanded second position.

The first balloon portion 116 includes a proximal end portion 170 and a distal end portion 172, and the second balloon portion 118 includes a proximal end portion 174 and a distal end portion 176.

The proximal end portion 170 of the first balloon portion 116 can be annular (given that the outer shape of outer first tubular portion 112 is cylindrical), is attached relative to the outer first tubular portion 112, and is configured to facilitate formation of a fluid tight seal to prevent the liquid received in the first interior cavity 160 from escaping.

The distal end portion 172 of the first balloon portion 116 can also be annular (given that the outer shape of the valve 20 is cylindrical), is attached relative to the valve 20 (which is attached relative to the inner second tubular portion 114, and is configured to facilitate formation of a fluid tight seal to prevent the liquid received in the first interior cavity 160 from escaping.

The proximal end portion 174 of the second balloon portion 118 can be annular (given that the outer shape of the valve 20 is cylindrical), is attached relative to the valve 20, and is configured to facilitate formation of a fluid tight seal to prevent liquid received in the second interior cavity 162 from escaping.

The distal end portion 176 of the second balloon portion 118 can be annular (given that the outer shape of the inner second tubular portion 114 is cylindrical), is attached relative to the inner second tubular portion 114, and is configured to facilitate formation of a fluid tight seal to prevent the liquid received in the second interior cavity 162 from escaping.

So long as a fluid tight seal is formed therebetween, the proximal end portion 170 can be directly or indirectly attached to the outer first tubular portion 112, the distal end portion 172 can be directly or indirectly attached to the valve 20, the proximal end portion 174 can be directly or indirectly attached to the valve 20, and the distal end portion 176 can be directly or indirectly attached to the inner second tubular portion 114. The direct or indirect attachment can be effectuated using adhesives, heat welding, mechanical fasteners, and/or complimentary surface configurations formed on mating components.

Furthermore, while the outer first tubular portion 112, the inner second tubular portion 114, and the valve 20 have cylindrical outer shapes, these components can have different outer shapes, and the proximal end portion 170, the distal end portion 172, the proximal end portion 174, and the distal end portion 176 can be configured to compliment these different shapes. Furthermore, the valves 20, 20', 20", 20''', and 108 in the inflatable bone tamp 110 can be used in similar fashion to use in the inflatable bone tamp 10 to facilitate sequential inflation of the first balloon portion 116 and the second balloon portion 118.

During use thereof, first balloon portion 116 and the second balloon portion 118 of the inflatable bone tamp 110 can be positioned in a surgical area. Thereafter, the liquid is first pumped through the passageway 134 formed in the outer first tubular portion 112 by the third pump. The liquid exits the passageway 134 and enters the first interior cavity 160 of the first balloon portion 116 to expand the first balloon portion 116 from the contracted first position to the expanded second position. After the pressure of the liquid reaches the threshold pressure, the first balloon portion 116 stops expanding and the liquid is forced through the perforations 82 to enter the second interior cavity 162 of the second balloon portion 118 to expand the second balloon portion 118 from the contracted first position to the expanded second position. As such, the first balloon portion 116 and the second balloon portion 118 are inflated sequentially, with the first balloon portion 116 being inflated first and the second balloon portion 118 being inflated second via use of the valve 20. The valves 20', 20", 20''', and 108 can be used in identical fashion to sequentially inflate the first balloon portion 116 and the second balloon portion 118. Furthermore, the expanded second position of the second balloon portion 118 can vary as needed to afford different amounts of expansion thereof.

After use of the inflatable bone tamp 110 is nearing completion, the third pump can be reversed to pump liquid from the first interior cavity 160 of the first balloon portion 116 via the passageway 134 of the outer first tubular portion 112, and the fourth pump can be used to pump liquid from the second interior cavity 162 of the second balloon portion 118 via the apertures 146 and the passageway 144 of the inner second tubular portion 114. After being deflated, the inflatable bone tamp 110 can be removed from the surgical area.

The inflatable bone tamps 10 and 110 can be used to facilitate use of surgical solutions to ameliorate spinal disease or injuries where a wedge fracture or a collapsed endplate of a vertebral body has occurred. To illustrate, a wedge fracture is a compression fracture of a vertebral body that causes a lateral portion, an anterior portion, or a posterior portion of a corresponding endplate to be displaced from its normal configuration, and such displacement causes misalignment of the endplate with the opposing endplate across the disc space. The misalignment of the opposing endplates can cause misalignment of the corresponding adjacent vertebrae with respect to one another, and an anatomically-correct relationship between the adjacent vertebrae is needed to ameliorate a wedge fracture. As discussed below, the sequential inflation of the inflatable bone tamps 10 and 110 affords restoration of the adjacent vertebrae into an anatomically-correct relationship by accommodating shape of the displaced portion of the endplate.

To illustrate, the inflatable bone tamp 10 can be positioned such that the first balloon portion 16 at and adjacent to a distal end of the inflatable bone tamp 10 is positioned adjacent to a displaced portion of an endplate and the second balloon portion 18 is positioned adjacent to a non-displaced portion of the endplate, where the first balloon portion 16 is inflated first and the second balloon portion 18 is inflated second as needed to restore an anatomically-corrected relationship between the adjacent vertebrae. And to illustrate, the inflatable bone tamp 110 can be positioned such that the second balloon portion 118 at and adjacent to a distal end of the inflatable bone tamp 110 is positioned adjacent to a displaced portion of an endplate and the first balloon portion 116 is positioned adjacent to a non-displaced portion of the endplate, where the first balloon portion 116 is inflated first and the second balloon portion 118 is inflated second as needed to restore an anatomically-corrected relationship between the adjacent vertebrae.

Figure 9:
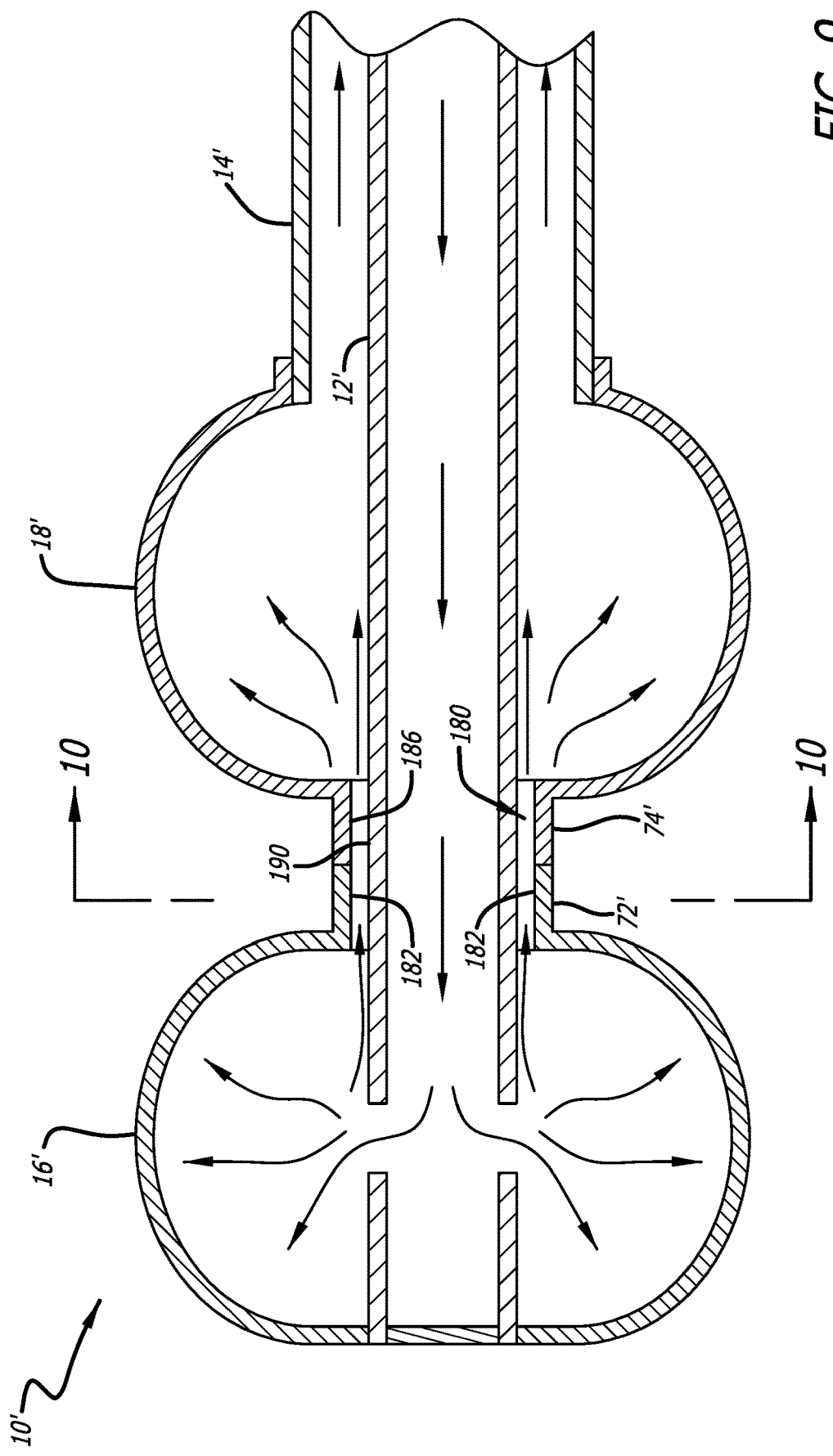
FIG. 9 is a side, cross-sectional, elevational view that illustrates yet another inflatable bone tamp including a first balloon portion and a second balloon portion that are sequentially inflatable.

The inflatable bone tamps 10 and 110 can also be configured to such that the need for the valves 20, 20', 20'', 20''', and 108 is obviated. Rather than using the valves 20, 20', 20'', and 20''', and 108, valves can be formed by and incorporated in the other componentry of the inflatable bone tamps 10 and 110. To illustrate, a modified version of the inflatable bone tamp 10 is depicted in FIG. 9 as inflatable bone tamp 10'. The inflatable bone tamp 10' includes an inner first tubular (or shaft) portion 12', an outer second tubular (or shaft) portion 14', and a first balloon portion 16'. The first balloon portion 16' and the second balloon portion 18' can be made of elastomeric materials facilitating expansion and contraction thereof. Rather than using the valves 20, 20', 20'', 20''', or 108, valves 180 can be formed between the inner first tubular portion 12', and portions of the first balloon portion 16' and/or the second balloon portion 18'. To illustrate, the first balloon portion 16' includes a proximal end portion 72', and the second balloon portion 18' includes a distal end portion 74'. The proximal end portion 72' and the distal end portion 74' can be contacted to the inner first tubular portion 12'. Furthermore, indentations can be formed in the inner first tubular portion 12', the proximal end portion 72', and/or the distal end portion 74', that afford fluid communication between a first interior cavity 60' of the first balloon portion 16' and a second interior cavity 62' of the second balloon portion 18'. Similarly, apertures can be formed through the proximal end portion 72' and the distal end portion 74' that afford fluid communication between the first interior cavity 60' of the first balloon portion 16' and the second interior cavity 62' of the second balloon portion 18'. But for the channels created by these indentations and/or these apertures, fluid-tight seals are formed between the inner first tubular portion 12', and the proximal end portion 72' and the distal end portion 74'. As such, the indentations and the apertures serve form the valves 180 that restrict flow between the first interior cavity 60' and the second interior cavity 62'. Furthermore, the indentions and the apertures can have configurations like the perforations 82 and 82'.

Figure 10:
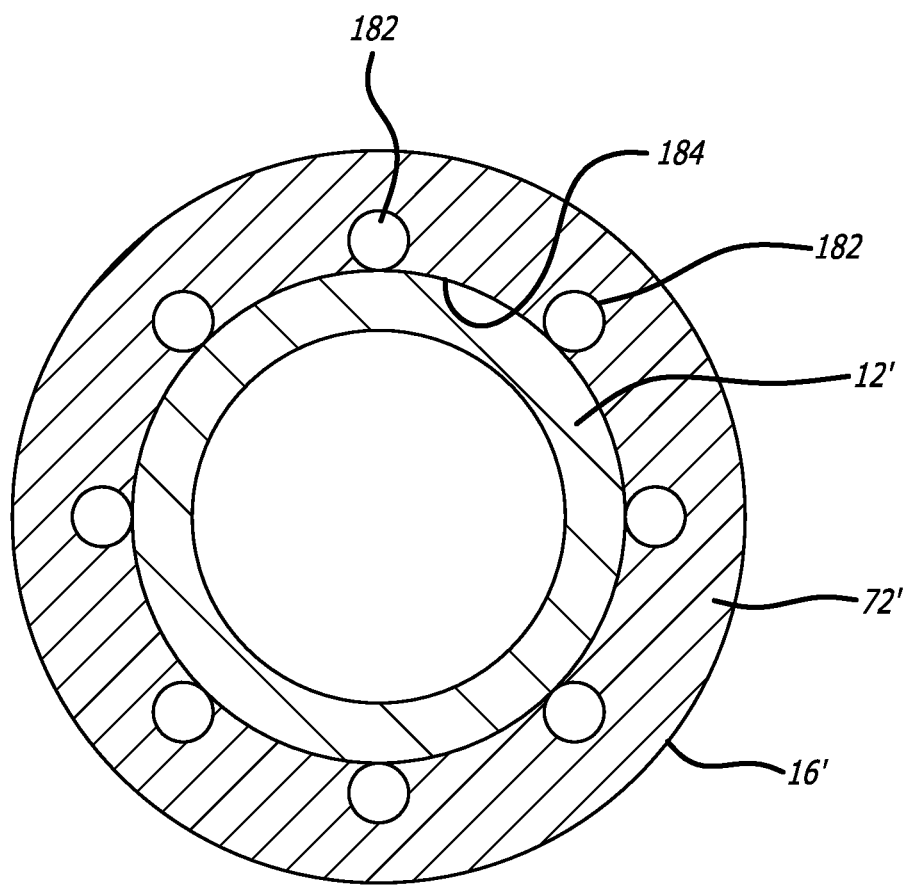
FIG. 10 is a side, cross-sectional, elevational view that illustrates a valve formed by an inner tubular portion and portions of the first balloon portion and/or the second balloon portion.

As depicted in FIG. 10, indentations 182 are formed along an inner surface 184 of the proximal end portion 72'. And similar indentations 186 can be formed along an inner surface (not shown) of the distal end portion 74'. Furthermore, to form a channel affording fluid communication between the first interior cavity 60' and the second interior cavity 62', the indentations 182 and the indentations 186 can be aligned with one another (FIG. 9), and complete perimeters (FIG. 10) can be formed between an outer surface 190 of the inner first tubular portion 12', and the indentations 182 and the indentations 186. Rather than or in addition to the indentations 182 and 186 in the proximal end portion 72' and the distal end portion 74', indentations can be formed in the outer surface 190 of the inner first tubular portion 12', and/or apertures (with complete perimeters) can be formed through the proximal end portion 72' and the distal end portion 74' to afford such fluid communication.

These indentations and/or apertures can be used to sequentially inflate the first balloon portion 16' and the second balloon portion 18' of the inflatable bone tamp 10 in similar fashion to the inflatable bone tamp 10. Similarly, these indentations and/or apertures can be used in a modified version of the inflatable bone tamp 110 that likewise afford such sequential inflation.

It should be understood that various aspects disclosed herein may be combined in different combinations than the combinations specifically presented in the description and the accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

What is claimed is:

1. An inflatable bone tamp comprising:
    an inner first tubular portion including a first passageway therethrough, and extending between a first proximal end and an opposite first distal end, the inner first tubular portion including at least one aperture adjacent the first distal end;
    an outer second tubular portion including a second passageway therethrough, and extending between a second proximal end and an opposite second distal end, the inner first tubular portion extending through the second passageway;
    a valve including an outer surface, a first side, an opposite second side, an aperture extending between the first side and the second side, and various perforations extending between the first side and the second side, the inner first tubular portion being received through the aperture;
    a first balloon portion including a first cavity, a first distal end portion, and a first proximal end portion, the first distal end portion being attached relative to the inner first tubular portion, and the first proximal end portion being attached relative to the outer surface of the valve; and
    a second balloon portion including a second cavity, a second distal end portion, and a second proximal end portion, the second distal end portion being attached relative to the outer surface of the valve, and the second proximal end portion being attached relative to the outer second tubular portion;

wherein the first cavity and the second cavity communicate with one another via the various perforations in the valve, wherein a liquid pumped through the first passageway can enter the first cavity via the at least one aperture of the inner first tubular portion and can expand the first balloon portion from a first contracted position to a first expanded position, wherein the valve limits passage of the liquid from the first cavity to the second cavity through the various perforations until a threshold pressure of the liquid is reached in the first cavity, and wherein the fluid entering the second cavity via the various perforations in the valve can expand the second balloon portion from a second contracted position to a second expanded position.

2. The inflatable bone tamp of claim 1, wherein the threshold pressure can range from 50 to 300 psi.

3. The inflatable bone tamp of claim 1, wherein the various perforations are each formed by a first opening in the first side of the valve, a second opening in the second side of the valve, and a pathway extending between the first opening and the second opening.

4. The inflatable bone tamp of claim 3, wherein the first opening is larger than the second opening, and the pathway is tapered between the first opening and the second opening.

5. The inflatable bone tamp of claim 3, wherein the pathway has a convoluted path between the first opening and the second opening.

6. The inflatable bone tamp of claim 1, wherein the valve is made from foam, and the various perforations are formed through an open cell structure of the foam.

7. The inflatable bone tamp of claim 1, wherein each of the first balloon portion and the second balloon portion have toroidal shapes surrounding portions of the inner first tubular portion.

8. The inflatable bone tamp of claim 1, wherein a first fluid-tight seal is formed between the first distal end portion of the first balloon portion and the inner first tubular portion, a second fluid-tight seal is formed between the first proximal end portion of the first balloon portion and the outer surface of the valve, a third fluid-tight seal is formed between the second distal end portion of the second balloon portion and the outer surface of the valve, and a fourth fluid-tight seal is formed between the second proximal end portion and the outer second tubular portion.

9. An inflatable bone tamp comprising:
an outer first tubular portion including a first passageway therethrough, and extending between a first proximal end and an opposite first distal end;
an inner second tubular portion including a second passageway therethrough, and extending between a second proximal end and an opposite second distal end, the inner second tubular portion extending through the first passageway, and the inner second tubular portion including at least one aperture adjacent the first distal end;
a valve including an outer surface, a first side, an opposite second side, an aperture extending between the first side and the second side, and various perforations extending between the first side and the second side, the inner second tubular portion being received through the aperture;
a first balloon portion including a first cavity, a first proximal end portion, and a first distal end portion, the first proximal end portion being attached relative to the outer first tubular portion, and the first distal end portion being attached relative to the outer surface of the valve; and
a second balloon portion including a second cavity, a second proximal end portion, and a second distal end portion, the second proximal end portion being attached relative to the outer surface of the valve, and the second distal end portion being attached relative to the inner second tubular portion;

wherein the first cavity and the second cavity communicate with one another via the various perforations in the valve, wherein a liquid pumped through the first passageway can enter the first cavity and can expand the first balloon portion from a first contracted position to a first expanded position, wherein the valve limits passage of the liquid from the first cavity to the second cavity through the various perforations until a threshold pressure of the liquid is reached in the first cavity, and wherein the fluid entering the second cavity via the various perforations in the valve can expand the second balloon portion from a second contracted position to a second expanded position.

10. The inflatable bone tamp of claim 9, wherein the threshold pressure can range from 50 to 300 psi.

11. The inflatable bone tamp of claim 9, wherein the various perforations are each formed by a first opening in the first side of the valve, a second opening in the second side of the valve, and a pathway extending between the first opening and the second opening.

12. The inflatable bone tamp of claim 11, wherein the first opening is larger than the second opening, and the pathway is tapered between the first opening and the second opening.

13. The inflatable bone tamp of claim 11, wherein the pathway has a convoluted path between the first opening and the second opening.

14. The inflatable bone tamp of claim 9, wherein the valve is made from foam, and the various perforations are formed through an open cell structure of the foam.

15. The inflatable bone tamp of claim 9, wherein each of the first balloon portion and the second balloon portion have toroidal shapes surrounding portions of the inner first tubular portion.

16. The inflatable bone tamp of claim 9, wherein a first fluid-tight seal is formed between the first proximal end portion of the first balloon portion and the outer first tubular portion, a second fluid-tight seal is formed between the first distal end portion of the first balloon portion and the outer surface of the valve, a third fluid-tight seal is formed between the second proximal end portion of the second balloon portion and the outer surface of the valve, and a fourth fluid-tight seal is formed between the second distal end portion and the inner second tubular portion.

17. An inflatable bone tamp comprising:
an inner first tubular portion including a first passageway therethrough, and extending between a first proximal end and an opposite first distal end, the inner first tubular portion including at least one aperture adjacent the first distal end;
an outer second tubular portion including a second passageway therethrough, and extending between a second proximal end and an opposite second distal end, the inner first tubular portion extending through the second passageway;

a valve including an outer surface, a first side, an opposite second side, an aperture extending between the first side and the second side, and various perforations extending between the first side and the second side, the inner first tubular portion being received through the aperture;

a first balloon portion having a first distal end portion and a first proximal end portion, the first distal end portion being attached relative to the inner first tubular portion, and the first proximal end portion being attached relative to the outer surface of the valve; and a second balloon portion having a second distal end portion and a second proximal end portion, the second distal end portion being attached relative to the outer surface of the valve, and the second proximal end portion being attached relative to the outer second tubular portion;

wherein interiors of the first balloon portion and the second balloon portion communicate with one another via the various perforations in the valve, wherein a liquid pumped through the first passageway can enter the interior of the first balloon portion via the at least one aperture of the inner first tubular portion and can expand the first balloon portion from a first contracted position to a first expanded position, wherein the valve limits passage of the liquid between the interiors of the first balloon portion and the second balloon portion through the various perforations until a threshold pressure of the liquid is reached in the interior of the first balloon portion, and wherein the fluid entering the interior of the second balloon portion via the various perforations in the valve can expand the second balloon portion from a second contracted position to a second expanded position.

18. The inflatable bone tamp of claim 17, wherein the threshold pressure can range from 50 to 300 psi.

19. The inflatable bone tamp of claim 17, wherein the various perforations are each formed by a first opening in the first side of the valve, a second opening in the second side of the valve, and a pathway being one of tapered and convoluted extending between the first opening and the second opening.

20. The inflatable bone tamp of claim 17, wherein the valve is made from foam, and the various perforations are formed through an open cell structure of the foam.

* * * * *